United States Patent [19]

Linder

[11] Patent Number: 5,069,900

[45] Date of Patent: Dec. 3, 1991

[54] BORONIC ACID ADDUCTS OF TECHNETIUM-$^{99m}$ DIOXIME-IMINE COMPLEXES

[75] Inventor: Karen E. Linder, Highland Park, N.J.

[73] Assignee: E. R. Squibb & Sons, Inc., Princeton, N.J.

[21] Appl. No.: 398,880

[22] Filed: Aug. 28, 1989

[51] Int. Cl.[5] ...................... A61K 43/00; A61K 49/02

[52] U.S. Cl. ....................................... 424/1.1; 534/14; 252/645

[58] Field of Search ...................... 424/1.1; 534/10, 14

[56] References Cited

U.S. PATENT DOCUMENTS

| | | | |
|---|---|---|---|
| 4,387,087 | 6/1983 | Deutsch et al. | 424/1.1 |
| 4,419,339 | 12/1983 | Neirinckx | 424/1.1 |
| 4,615,876 | 10/1986 | Troutner et al. | 424/1.1 |
| 4,705,849 | 11/1987 | Nunn et al. | 534/14 |
| 4,714,605 | 12/1987 | Feld et al. | 424/1.1 |
| 4,795,626 | 1/1989 | Deutsch et al. | 424/1.1 |
| 4,871,836 | 10/1989 | Francesconi et al. | 534/10 |

*Primary Examiner*—Richard D. Lovering
*Assistant Examiner*—John M. Covert
*Attorney, Agent, or Firm*—Theodore R. Furman, Jr.

[57] ABSTRACT

Boronic acid adducts of technetium-$^{99m}$ imine-dioxime complexes are useful for imaging the myocardium, hepatobiliary system, brain and blood pool in humans and other mammalian species.

21 Claims, No Drawings

BORONIC ACID ADDUCTS OF TECHNETIUM-$^{99m}$ DIOXIME-IMINE COMPLEXES

FIELD OF THE INVENTION

The present invention relates to neutral technetium-$^{99m}$ boron capped imine-oxime complexes which are useful as radiodiagnostic agents.

BACKGROUND OF THE INVENTION

U.S. Pat. No. 4,705,849 discloses a series of technetium-$^{99m}$ complexes having the formula $^{99m}TcX(Y)_3BR$ wherein X is an anion, Y is a vicinal dioxime and BR is a boron derivative. The complexes of U.S. Pat. No. 4,705,849 are prepared by a template synthesis reaction in which the ligands that are bound to the technetium atom are formed in an in-situ reaction between boronic acid, three vicinal dioximes, a halide ion, a reducing agent and pertechnetate. It has now been discovered that a novel and unexpected product is formed when the above reaction conditions are changed. These changes include the use of a new reducing agent such as triphenylphosphine which increases the yield of the new complexes of the present invention.

BRIEF DESCRIPTION OF THE INVENTION

Boronic acid adducts of technetium-$^{99m}$ imine-oxime complexes having the formula $$^{99m}TcXY(Z)_2BR_3$$

are useful as imaging agents in humans and other mammalian species. In formula I and throughout the specification, the above symbols are as defined below.

X is an anion selected from the group consisting of fluoro, chloro, iodo, hydroxy, bromo or isothiocyanate.

Y is an imine-oxime having the formula

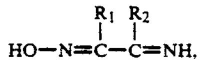

II wherein $R_1$ and $R_2$ are each independently hydrogen, halogen, alkyl, aryl, amino or taken together a 5 or 6-membered nitrogen, oxygen, or sulfur containing heterocycle, or together $R_1$ and $R_2$ are $-(CR_8R_9)_n-$w wherein n is 3, 4, 5 or 6 and $R_8$ and $R_9$ are each independently hydrogen or alkyl;

Z is a vicinal dioxime having the formula

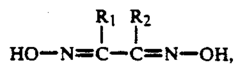

III where $R_1$ and $R_2$ are defined as above; $BR_3$ is a boron derivative wherein $R_3$ is hydroxy, alkyl, alkenyl, cycloalkyl, cycloalkenyl, alkoxy, carboxyalkyl (preferably having 2 to 19 carbons), carboxyalkenyl (preferably having 4 to 19 carbons), hydroxyalkyl, hydroxyalkenyl, alkoxyalkyl, alkoxyalkenyl, haloalkyl, haloalkenyl, aryl, arylalkyl or $(R_4R_5N)$-alkyl wherein $R_4$ and $R_5$ are each independently hydrogen, alkyl, or arylalkyl, or $R_4$ and $R_5$ when taken together with the nitrogen atom to which they are attached form a 5 or 6-membered nitrogen containing heterocycle.

Listed below are definitions of terms used to describe the complexes of this invention. These definitions apply to the terms as they are used throughout the specification (unless they are otherwise limited in specific instances) either individually or as part of a larger group.

The terms "alkyl" and "alkoxy" refer to both straight and branched chain groups. Those groups having 1 to 10 carbon atoms are preferred.

The term "alkenyl" refers to both straight and branched chain groups. Those groups having 2 to 10 carbon atoms are preferred.

The term "aryl" refers to phenyl and substituted phenyl. Preferred are phenyl and phenyl substituted with 1, 2 or 3 alkyl, haloalkyl, aminoalkyl, alkylaminoalkyl, dialkylaminoalkyl, alkoxy, alkoxyalkyl, halogen, amino, hydroxy, or formyl groups. Additional exemplary aryl groups for the instance wherein $R_3$ is aryl include 3-(5-dimethylamino-1-naphthalenesulfonylamino)phenyl, 3-[4-[3'-phenyl-2'-pyrazolin-1,1'-yl]benzenesulfonyl-amino]phenyl, 3-(pyrenesulfamido)-phenyl, 3-[4-(4-dimethylamino-1-naphthylazo)-3-(methoxyphenyl-sulfamido)]phenyl, 3-[4(4-dimethylamino-1-phenylazo)phenylthioureido]phenyl.

Preferred "cycloalkyl" and "cycloalkenyl" groups are those having 5,6 or 7 carbon atoms. The terms include those groups substituted with alkyl, alkoxy, aryl, carboxyalky, arylalkyl or $(R_4R_5N)$-alkyl groups.

The terms "halide", "halo" and "halogen" refer to fluorine, chlorine, bromine and iodine.

The expression "5 or 6-membered nitrogen containing heterocycle" refers to all 5 or 6-membered rings containing at least one nitrogen atom. Exemplary aliphatic groups are dehydro - derivatives of a compound having the formula

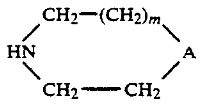

wherein m is 0 or 1 and A is oxygen, sulfur, N—$R_6$ or CH—$R_6$ wherein $R_6$ is hydrogen, alkyl, aryl or arylalkyl. Such groups include pyrrolidinyl, piperidinyl, morpholinyl, piperazinyl, 4-alkylpiperazinyl, 4-alkylpiperidinyl, and 3-alkylpyrrolidinyl groups. Also included within the expression "5 or 6-membered nitrogen containing heterocycle" are aromatic groups. Exemplary aromatic groups are pyrrolyl, imidazolyl, oxazolyl, pyrazolyl, pyridinyl, and pyrimidinyl groups. The above groups can be linked via a hetero atom or a carbon atom.

The expression "5 or 6-membered nitrogen or oxygen, sulfur containing heterocycle" refers to all 5 and 6-membered rings containing at least one nitrogen, sulfur or oxygen atom. Exemplary groups are those described above under the definition of the expression "5 or 6-membered nitrogen containing heterocycle". Additional exemplary groups are 1,4-dioxanyl and furanyl.

DETAILED DESCRIPTION OF THE INVENTION

Preparation of the complexes of this invention can best be accomplished using technetium-$^{99m}$ in the form of pertechnetate ion. The pertechnetate ion can be obtained from commercially available generators; such technetium is in the +7 oxidation state. The generation of pertechnetate ion using this type of generator is well known in the art and is described in more detail in U.S. Pat. Nos. 3,369,121 and 3,920,995. These generators are usually eluted with saline solution and the pertechnetate ion is obtained as the sodium salt.

To prepare the complexes of this invention, pertechnetate ion (in the form of a salt) is combined with a source of an anion, and a boronic acid having the formula

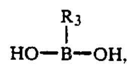

or a pharmaceutically acceptable salt thereof, or a boronic acid derivative such as

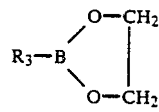

which can hydrolyze in solution to yield the boronic acid of Formula IV or a pharmaceutically acceptable salt thereof, and a dioxime having the formula

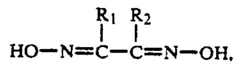

or a pharmaceutically accepted salt thereof.

The source of the anion is HX or NaX, or any acid or salt that can be dissociate in water to liberate the appropriate anion. The preferred anion is chloride; the source of chloride is the NaCl present in generator eluant, or HCl. It has been found that the chloride ion should be present in the reaction mixture in a concentration of about 0.3 to 2.5 molar.

The boronic acid derivative of formula IV should preferably be present in a concentration of about 5 to 200 millimolar. The dioxime of formula III should preferably be present in a concentration of 10 to 45 millimolar.

The formation of the complex proceeds best if the mixture of pertechnetate ion, source of anion, boronic acid and dioxime is heated at about 50° to 125° C. for about 5 minutes to about 60 minutes, preferably at about 70° to 110° C. for about 5 minutes to about 15 minutes. The reaction is preferably run in an aqueous or aqueous ethanolic medium at a pH of less than, or equal to about 4.

The reaction mixture must also contain a reducing agent. Triphenyl phosphine is the preferred reducing agent, and can be introduced into the reaction either as triphenyl phosphine, or as a pharmaceutically acceptable salt thereof. Stannous ion may also be used. Tin can be introduced in the form of a stannous salt such as a stannous halide (e.g., stannous chloride). The reducing agent should be present in a concentration of about 1.5 micromolar to about 25 millimolar.

Working with the technetium-99 isotope, the structure of one of the complexes of this invention has been investigated and is believed to be:

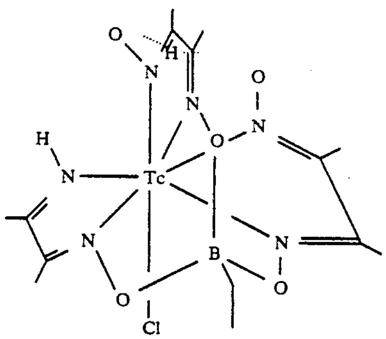

The imine-oxime moiety Y in the complexes of formula I can be formed during the template synthesis reaction that forms the complex. One could also add a source of ligand Y as well as dioxime X to the reaction mixture.

Various complexing agents (also known in the art as chelating agents) can be included as part of the complexing reaction. The complexing agent should, of course, be pharmaceutically acceptable. Exemplary complexing agents are diethylenetriamini-pentaacetic acid (DTPA), ethylene glycol-bis (β-aminoethyl ether)-N,N'-tetraacetic acid (EGTA), ethylenediamine tetraacetic acid (EDTA), citric acid, tartaric acid, malonic acid, etc.

The complexing reaction mixture can also include an accelerator (catalyst) which serves to improve the radiochemical purity (i.e., per cent of the radioactivity that is in the desired chemical form) of the product. Exemplary accelerators are the α-hydroxycarboxylic acids such as citric acid, tartaric acid, and malonic acid. A combination of DTPA and citric acid has been found to be preferred.

Because of the short half-life of technetium-$^{99m}$ (i.e. 6.02 hours), it is necessary to prepare the complexes of this invention at, or near, the site where they are to be used. A kit having all of the components, other than the pertechnetate ion, needed to prepare the boronic adducts of technetium-$^{99m}$ dioxime complexes of formula I is an integral part of this invention. Such a kit contains a source of anion, a boronic acid derivative of formula IV (or compounds which can react in situ to form such a derivative), or a pharmaceutically acceptable salt thereof, a dioxime of formula II, or a pharmaceutically acceptable salt thereof, and a reducing agent. It may optionally contain a complexing agent.

The kits of this invention can be formulated in aqueous solution. To optimize the stability of the kit, and to optimize the radiochemical purity of the labeled product, the pH of the kit should be adjusted to fall within the range of about 2.0 to about 4.0 using a pharmaceutically acceptable acid or base (e.g., hydrochloric acid or sodium hydroxide). Preferably, the pH of the kit will be about 3.0.

The complexes of this invention are useful as radiodiagnostic imaging agents. More specifically, they are useful for imaging the myocardium and the hepatobiliary system in mammalian species. Some of the complexes of this invention that are neutral at physiological pH (i.e, pH 7.4) are also useful for imaging the brain in mammalian species. [The charge of the complexes of this invention is determined by the sum of the charges of the organic groups ("$R_1$". "$R_2$", and "$R_3$") attached to the boron atom, imine-oxime, and the dioxime ligands.]

The complexes of this invention can be administered to a host by bolus intravenous injection. The size of the host, and the imaging system used, will determine the quantity of radioactivity need to produce diagnostic images. For a human host, the quantity of radioactivity injected is estimated to be in the range of about 5 to about 30 mCi of technetium-$^{99m}$.

The following examples are specific embodiments of this invention.

The sodium pertechnetate used in these examples is obtained by eluting a sterile technetium-$^{99m}$ generator with physiological saline.

As used in these examples, the yield is determined by Reverse-phase HPLC (High Pressure Liquid Chromatography) and is reported as the percentage of the total radioactivity eluted form the HPLC as the desired compound. Radioactivity was monitored and integrated throughout the run. The desired compounds of this invention were found to elute from the column at a retention time identical to that of authentic samples of standards of the complexes, prepared by alternate methods using the longed-lived isotope, $^{99}$Technetium.

EXAMPLE 1

$^{99m}$Technetium (chlorine) (3imino-2-butanone oxime) (2,3-butanedioxedioxime)$_2$phenyl boron To 10 ml of ethanol was added 25 mg of triphenyl phosphine, 18.8 mg of dimethyl glyoxime, 11.0 mg of phenyl boronic acid, and 6 drops of 2N HCl. An 0.5 ml aliquot of this solution was added to a 5 ml siliconized vial, followed by 0.5 ml (30 mCi) of $^{99m}$pertechnetate in physiological saline. The vial was sealed and heated to 100° C. for 15 minutes to yield 8.9% of the title compound as estimated by HPLC. The reaction also yielded TcCl (2,3-buanedione dioxime)$_3$ phenyl boron (TcCL (DMG)$_3$BPh) in 73% yield. The complexes were separated by HPLC.

EXAMPLE 2

$^{99m}$Technetium (chlorine) (3-imino-2-butanone oxime) (2,3-butanedionedioxime)$_2$(2-methyl propyl boron Following the procedure of Example 1, but substituted 2-methylpropyl boronic acid (10 mg) for the phenyl boronic acid, gave $^{99m}$Technetiium (chlorine) (3-imino-2-butanone oxime) (2,3-butanedionedioxime)$_2$(2-methyl-propyl) boron in 7.5% yield. The complex $^{99m}$Technetium (chlorine) (2,3-butanedionedioxime)$_3$ (2-methyl propyl) boron was also formed (70% yield). The complexes were separated by HPLC.

EXAMPLE 3

$^{99m}$Technetium (chlorine) (3-imino-2-butanone oxime)(2,3-butanedionedioxime)$_2$ cyclopentyl boron To 10 ml of ethanol was added 18.2 mg of dimethyl glyoxime, 25 mg of triphenyl phosphine, 10 mg of cyclopentane boronic acid, and 6 drops of 2N HCl. An aliquot of this solution (0.5 ml) was added to a siliconized 5 ml vial, followed by 25 μl of 2N HCl and 0.5 ml of normal saline containing 10 mCi of $^{99m}TcO_4$. The vial was sealed and heated at 100° C. for 15 minutes, yielding 6.8% of the complex $^{99m}$TcCl(3-imino-2-butanone oxime) (2,3-butanedione dioxime)$_2$cyclopentyl boron. The reaction also yielded TcCl(dimethyl glyoxime)$_3$ cyclopentyl boron (70% yield). The complexes were separated by HPLC.

EXAMPLE 4

$^{99m}$Technetium (chlorine) (1,2-cyclohexanedione-1-imine-2-oxime) (1,2-cyclohexanedione dioxime)$_2$ methyl boron To 10 ml of ethanol was added 15.3 mg of cyclohexanedione dioxime, 25.6 mg of triphenyl phosphine, 10.6 mg of methyl boronic acid, and 6 drops of 2N HCl. An aliquot of this solution (0.5 ml) was added to a siliconized 5 ml vial, followed by 25 μl of 2N HCl and 0.5 ml of a normal saline containing 10 mCi of $^{99m}TcO_4$. The vial was sealed, and heated at 100° C. for 15 minutes yielding 12% of the complex of $^{99m}$Tc(chlorine) (1,2-cyclohexanedione-1-imine-2-oxime) (1,2-cyclohexanedione dioxime)$_2$ methyl boron. The reaction also yielded $^{99m}$Tc(chlorine) (1,2-cyclohexanedione dioxime)$_3$ methyl boron (85.5% yield). The complexes were separated by HPLC.

EXAMPLE 5

$^{99}$TcCl(3-imino-2-butanone oxime)(2,3-butanedionedioxime)$_2$ethyl boron A mixture of $^{99}TcCl_3(CH_3CN)(PPh_3)_2$ (156 mg), dimethyl glyoxime (117 mg), and ethyl boronic acid (50 mg) in 15 ml of ethanol was heated gently under nitrogen with stirring for 1 hour. An equal volume of 1M HCl was added, and the solution was cooled to room temperature. The resulting red-brown precipitate was extracted into $CH_2Cl_2$, dried over sodium sulphate and chromatographed on a 1.5×5 cm silica gel column (flash chromatography grade). Elution with $CH_2Cl_2$ removed orange TcCl(DMG)$_3$BEt. The title compound was then eluted from the column with 80/20 $CH_2Cl_2/CH_3CH$. Recrystallization from $CH_2Cl_2$/hexanes yielded reddish/purple crystals, which were analyzed by X-ray crystallography, using techniques known to those skilled in the art.

EXAMPLE 6

$^{99}$TcCl(3-imino-2-butanone oxime)(2,3-butanedionedioxime)$_2$methyl boron The title compound was prepared following a procedure similar to that used in Example 5, but substituting methyl boronic acid for ethyl boronic acid. A sample of this complex co-eluted from a reverse phase HPCL column at a retention time identical to that of the $^{99m}$Tc complex $^{99m}$TcCl(3-imino-2-butanone oxime)(2,-3butanedionedioxime)$_2$methyl boron that was prepared as described in Example 4.

EXAMPLE 7

$^{99}$Tc(3-imino-2-butanone oxime)(2,3-butanedionedioxime)$_2$(2-methyl propyl) boron The title compound was prepared following a procedure similar to that used in Example 5, but substituting 2-methyl-propyl boronic acid for ethyl boronic acid. A sample of this complex co-eluted from a reverse-phase HPCL column at a retention time identical to that of the $^{99m}$Tc complex $^{99m}$TcCl(3-imino-2-butanone oxime)(2,3-butanedionedioxime)$_2$ (2-methyl-propyl) boron that was prepared as described in Example 2.

EXAMPLE 8

$^{99}$TcCl(3-imino-2-butanone oxime)(2,3-butanedionedioxime)$_2$phenyl boron

The title compound was prepared following a procedure similar to that used in Example 5, but substituting phenyl boronic acid for ethyl boronic acid. A sample of this complex co-eluted from a reverse-phase HPLC column at a retention time identical to that of the $^{99m}$Tc complex $^{99m}$TcCl(3-imino-2-butanone oxime)(2,3-butanedionedioxime)$_2$ phenyl boron that was prepared as described in Example 1.

What is claimed is:

1. A boronic acid adduct of technetium-$^{99m}$ imine-dioxime having the formula $$^{99m}TcX(Y)(Z)_2BR_3 \quad (I)$$

where X is selected from the group consisting of fluoro, chloro, iodo, bromo, hydroxy and isothiocyanate; Y is an imine-oxime having the formula $$HO-N=\overset{R_1}{\overset{|}{C}}-\overset{R_2}{\overset{|}{C}}=NH, \quad II$$

wherein $R_1$ and $R_2$ are each independently hydrogen, halogen, alkyl, aryl, amino or taken together a 5 or 6-membered oxygen, nitrogen or sulfur containing heterocycle, or together $R_1$ and $R_2$ are $-(CR_8R_9)_n-$ wherein n is 3, 4, 5 or 6 and $R_8$ and $R_9$ are each independently hydrogen or alkyl;

Z ia a vicinal dioxime having the formula $$HO-N=\overset{R_1}{\overset{|}{C}}-\overset{R_2}{\overset{|}{C}}=N-OH, \quad III$$

where $R_1$ and $R_2$ are defined as they are in formula II above; and $BR_3$ is a boron derivative wherein $R_3$ is hydroxy, alkyl, alkenyl, cycloalkyl, cycloalkenyl, alkoxy, hydroxyalkyl, aryl, arylalkyl or a 5 or 6-membered nitrogen containing heterocycle.

2. A boronic acid adduct in accordance with claim 1, wherein z is dimethyl glyoxime, 1,2-cyclohexanedione dioxime, 1,2-cyclopentanedione dioxime, 1-2-ethanedione dioxime, α-furyldioxime, or 3-methyl-1,2-cyclopentanedione dioxime.

3. A boronic acid adduct in accordance with claim 1, wherein Z is the vicinal dioxime dimethylglyoxime.

4. A boronic acid adduct in accordance with claim 1, wherein $R_3$ is hydroxy, alkyl, alkenyl, cycloalkyl, cycloalkenyl, alkoxy, hydroxyalkyl, aryl, arylalkyl, or a 5 to 6-membered nitrogen, containing heterocycle.

5. A boronic acid adduct in accordance with claim 1, wherein the boronic acid derivative $BR_3$ is $B-CH_3$.

6. A boronic acid adduct in accordance with claim 1, wherein the boronic acid derivative $BR_3$ is B-(2-methyl propyl).

7. A boronic acid adduct in accordance with claim 1, wherein the boronic acid derivative $BR_3$ is B-cyclopentyl.

8. A boronic acid adduct in accordance with claim 1, wherein the boronic acid derivative $BR_3$ is B-phenyl.

9. A boronic acid adduct in accordance with claim 1, wherein X is chloride ion.

10. The boronic acid adduct in accordance with claim 1 $^{99m}$Technetium(chlorine) (3-imino-2-butanone oxime) (2,3-butanedionedioxime)$_2$ (2-methyl propyl) boron.

11. The boronic acid adduct in accordance with claim 1 $^{99m}$Technetium(chlorine) (3-imino-2-butanone oxime) (2,3-butanedionedioxime)$_2$ (phenyl boron.

12. The boronic acid adduct in accordance with claim 1 $^{99m}$Technetium(chlorine) (3-imino-2-butanone oxime) (2,3-butanedionedioxime)$_2$ cyclopentyl boron.

13. The boronic acid adduct in accordance with claim 1, $^{99m}$Technetium(chlorine) (1,2-cyclohexanedione-1-imine-2-oxime) (1,2-cyclohexanedione dioxime)$_2$ methyl boron.

14. A kit suitable for labeling with technetium-$^{99m}$, said kit comprising:

(i) a source of anion;

(ii) a boronic acid derivative, or compounds which can react in situ to form a boronic acid derivative, having the formula $$HO-\overset{R_3}{\overset{|}{B}}-OH$$

or a pharmaceutically acceptable salt thereof, wherein $R_3$ is hydroxy, alkyl, alkenyl, cycloalkyl, cycloalkenyl, alkoxy, carboxyalkyl, carboxyalkenyl, hydroxyalkyl, hydroxyalkenyl, alkoxyalkyl, alkoxyalkenyl, haloalkyl, haloalkenyl, aryl, arylalkyl or $R_4R_5N$-alkyl and $R_4$ and $R_5$ are each independently hydrogen, alkyl, or arylalkyl, or $R_4$ and $R_5$ when taken together with nitrogen atom to which they are attached form a 5 or 6-membered nitrogen containing heterocycle;

a dioxime having the formula $$HO-N=\overset{R_1}{\overset{|}{C}}-\overset{R_2}{\overset{|}{C}}=N-OH, \quad (iii)$$

or a pharmaceutically acceptable salt thereof, wherein $R_1$ and $R_2$ are each independently hydrogen, halogen, alkyl, aryl, amino or a 5 or 6-membered nitrogen, oxygen or sulfur containing heterocycle, or together $R_1$ and $R_2$ are $-(CR_8R_9)n-$ wherein n is 3, 4, 5 or 6 or $R_8$ and $R_9$ are each independently hydrogen or alkyl; an imine-dioxime having the formula $$OH-N=\underset{R_1}{\underset{|}{C}}-\underset{R_2}{\underset{|}{C}}=NH \quad (iv)$$

wherein $R_1$ and $R_2$ are as defined above and (V) a reducing agent.

15. A kit in accordance with claim 14, wherein the source of anion is a source of halide.

16. A kit in accordance with claim 14, wherein the source of anion is a source of chloride or bromide.

17. A kit in accordance with claim 14, wherein the dioxime is dimethyl glyoxime, 1,2-cyclohexanedione dioxime, 1,2-ethanedione dioxime or α-furyldioxime.

18. A kit in accordance with claim 14, wherein the dioxime is dimethyl glyoxime.

19. A kit in accordance with claim 14, wherein the dioxime is 1,2-cyclohexanedione dioxime.

20. A kit in accordance with claim 14, wherein the reducing agent is triphenylphosphine.

21. A kit in accordance with claim 14 wherein the reducing agent is stannous chloride.

* * * * *